(12) United States Patent
Patil

(10) Patent No.: US 10,797,336 B2
(45) Date of Patent: Oct. 6, 2020

(54) APPARATUS AND A METHOD FOR IN-VIVO POWER GENERATION

(71) Applicant: Tarkeshwar Chandrakant Patil, Mumbai (IN)

(72) Inventor: Tarkeshwar Chandrakant Patil, Mumbai (IN)

(73) Assignee: Tarkeshwar Chandrakant Patil, Mumbai, Maharashtra (IN)

( * ) Notice: Subject to any disclaimer, the term of this patent is extended or adjusted under 35 U.S.C. 154(b) by 1012 days.

(21) Appl. No.: 14/280,341

(22) Filed: May 16, 2014

(65) Prior Publication Data

US 2015/0064579 A1   Mar. 5, 2015

(30) Foreign Application Priority Data

Aug. 28, 2013   (IN) .......................... 2808/MUM/2013

(51) Int. Cl.
    *H01M 8/16*   (2006.01)
    *A61M 27/00*   (2006.01)
    *A61M 37/00*   (2006.01)

(52) U.S. Cl.
    CPC .......... *H01M 8/16* (2013.01); *A61M 37/0015* (2013.01); *Y02E 60/527* (2013.01)

(58) Field of Classification Search
    CPC ...... H01M 8/16; H01M 8/04; H01M 8/04298; A61M 27/00; A61M 27/006; C12Q 1/26; C12Q 1/32
    See application file for complete search history.

(56) References Cited

U.S. PATENT DOCUMENTS

| | | | | |
|---|---|---|---|---|
| 3,262,869 A * | 7/1966 | Belasco | .................... | C01B 5/00 205/343 |
| 6,561,978 B1 * | 5/2003 | Conn | .................... | A61B 5/0031 600/309 |
| 2006/0057388 A1 * | 3/2006 | Jin | ........................... | B82B 3/00 428/408 |
| 2007/0190394 A1 * | 8/2007 | Kabumoto | ........ | H01M 8/04186 429/410 |
| 2007/0264534 A1 * | 11/2007 | Zhang | ....................... | C12P 3/00 429/2 |

(Continued)

OTHER PUBLICATIONS

"The New Requirements in Chemistry", W. Lash Miller, University of Toronto, p. 42, 1905.*

*Primary Examiner* — Kenneth J Douyette (57) ABSTRACT

An apparatus for an in-vivo power generation comprises a fuel convertor for converting glucose in a fluid to a hydrogen rich, low carbon fuel such as ethanol or methanol by the action of a bioenzyme on the glucose in the CSF. The fluid can be any one of cerebro spinal fluid, urine and glucose solution. The apparatus further comprises a biofuel cell comprising a cathode chamber and an anode chamber with a membrane assembly sandwiched between them. The membrane assembly comprises a cathode, an anode and a proton exchange membrane. The cathode is coated with an enzyme laccase, which enables extraction of oxygen when the fluid is passed through the cathode chamber. The oxygen from the cathode chamber and the hydrogen in the hydrogen rich fuel from the anode chamber diffuses through the proton exchange membrane and reacts at an ionic level to result in water and electrical power.

15 Claims, 7 Drawing Sheets

(56) References Cited

U.S. PATENT DOCUMENTS

| | | | | |
|---|---|---|---|---|
| 2008/0002472 | A1* | 1/2008 | Aleyraz | H01M 8/04559 |
| | | | | 365/185.19 |
| 2008/0044721 | A1* | 2/2008 | Heller | C12Q 1/26 |
| | | | | 429/2 |
| 2008/0274385 | A1* | 11/2008 | Creeth | H01M 4/8652 |
| | | | | 429/492 |
| 2009/0142649 | A1* | 6/2009 | Fernandez Lopez | C12N 11/14 |
| | | | | 429/401 |
| 2009/0297913 | A1* | 12/2009 | Zhang | H01M 4/92 |
| | | | | 429/499 |
| 2010/0099010 | A1* | 4/2010 | Niessen | H01M 6/34 |
| | | | | 429/506 |
| 2011/0121220 | A1* | 5/2011 | Curello | H01M 8/04208 |
| | | | | 251/330 |
| 2012/0156582 | A1* | 6/2012 | Tao | B82Y 30/00 |
| | | | | 429/454 |
| 2012/0244765 | A1* | 9/2012 | Huang | B63C 9/11 |
| | | | | 441/89 |

* cited by examiner

APPARATUS AND A METHOD FOR IN-VIVO POWER GENERATION

RELATED APPLICATION

This application claims priority under 35 U.S.C. § 119 to Indian Patent Application No. 2808/MUM/2013, filed on Aug. 28, 2013. The entire content of the foregoing application is explicitly incorporated herein by reference.

FIELD OF THE INVENTION

The present invention relates generally to an apparatus and method for in-vivo power generation. More specifically, the present invention relates to a biofuel cell using a fluid rich in glucose for electrical power generation.

BACKGROUND

The numbers of body implants have shown an exponential increase in their use. The traditional power sources used in the implants are lithium ion button batteries which need to be frequently recharged, and have a short lifetime of 2 years to 3 years and to replace them a surgery is required every time. These batteries also result in toxic contamination inside the body and result in fatalities.

US 2006/0020239 A1 delineates a cerebrospinal fluid (CSF) flow sensing device for sensing CSF flow through an implantable ventricular shunt. The sensing device is implanted within the CSF shunt, and includes a flow sensor to sense flow rate or shunt blockage. The sensing device is either placed within or adjacent the fluid path through the shunt. The sensing device transmits and sends the flow rate to an external monitoring device by wireless telemetry. The sensing device may be integrally formed as part of the shunt, or clamped onto apportion of the shunt, in which case the sensing device may be reusable. An external monitor receives the transmitted flow signal and presents information based on the flow signal. The disadvantage of the above described device is that the device has to be inductively powered or has to have it's own power supply.

There is therefore a need to mitigate the disadvantages associated with the devices explained above.

OBJECTIVE OF THE INVENTION

1. To achieve a power source which is biocompatible and used for in-vivo applications in the human body.
2. To achieve a nano scale biofuel cell with high power output and high efficiency.
3. To achieve using glucose present in the cerebrospinal fluid, glucose solution and urine for generation of electrical power.

SUMMARY

According to one aspect of the invention, there is disclosed an apparatus for in-vivo power generation. The apparatus comprises a fuel generator arranged to produce a hydrogen rich fuel from a fluid flowing through the fuel generator. The apparatus further comprises a biofuel cell comprising a first chamber and a second chamber separated by a membrane assembly, wherein a first electrode in the membrane assembly comprises a catalyst for enabling extracting oxygen from the fluid, the fluid being configured to flow through the first chamber and wherein the second chamber is arranged to receive the hydrogen rich fuel from the fuel generator. Electrical power is generated when the oxygen from the first chamber and hydrogen in the hydrogen rich fuel from the second chamber combine reactively.

According to another aspect of the invention, there is disclosed a method for in-vivo power generation using an in-vivo power generation apparatus comprising a fuel generator and a biofuel cell, wherein the biofuel cell comprises a first chamber and a second chamber and a membrane assembly disposed between the first chamber and the second chamber. The disclosed method comprises generating a hydrogen rich fuel from a fluid by passing the fluid through the fuel generator. The method further comprises extracting oxygen from the fluid by passing the fluid through the first chamber of the biofuel cell, wherein a catalyst in a first electrode in the membrane assembly enables extracting oxygen from the fluid. The method further comprises passing the hydrogen rich fuel through the second chamber in the biofuel cell. The method further comprises generating electrical power by a reaction occurring across the membrane assembly in the biofuel cell, the reaction occurring between the oxygen from the first chamber and hydrogen in the hydrogen rich fuel from the second chamber.

DETAILED DESCRIPTION

Figure 1:
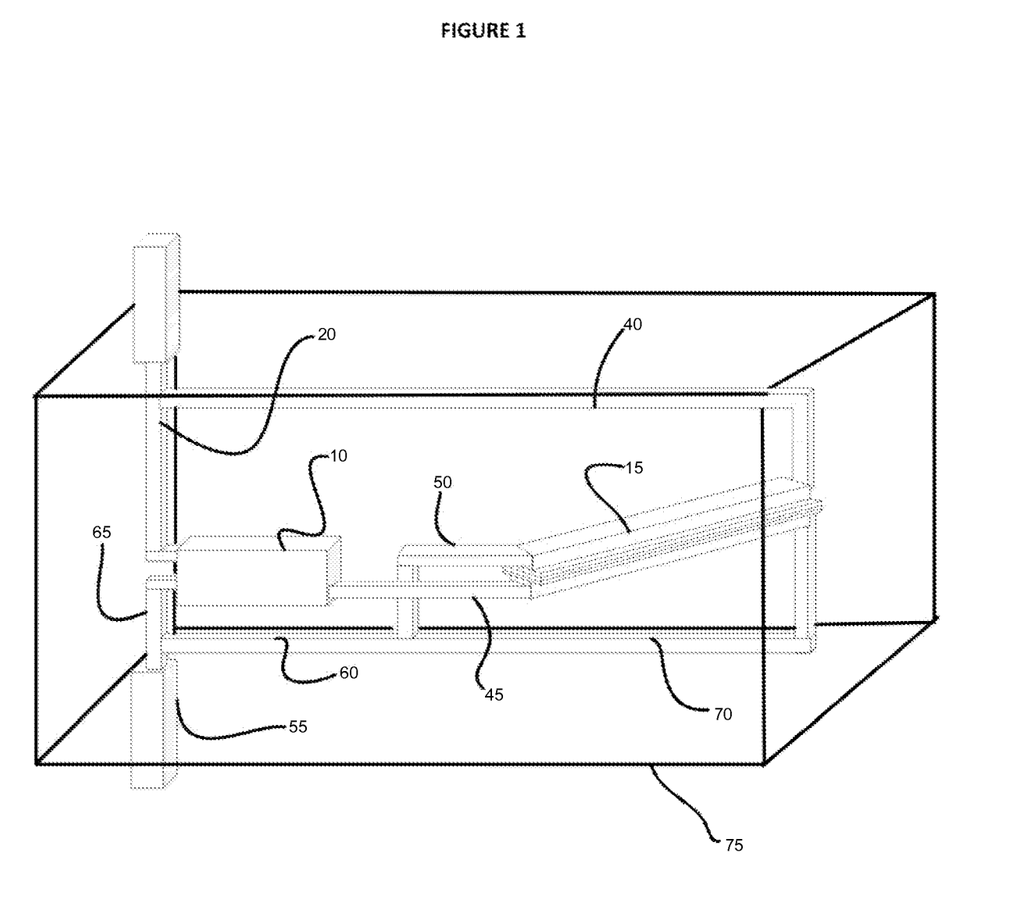
FIG. 1 is a schematic illustration of an apparatus for in-vivo power generation.

FIG. 1 is a schematic illustration of an apparatus 100 for in-vivo power generation. As illustrated in FIG. 1, the apparatus 100 for in-vivo power generation is used for powering medical implants inside human bodies and animals. The apparatus 100 uses raw materials for power generation from inside human bodies and animals, as will be described hereinafter.

The apparatus 100 comprises a fuel generator 10 and a biofuel cell 15. The fuel generator 10 is arranged to produce a hydrogen rich fuel from a fluid flowing through the same. The fuel generator 10 can be a low carbon fuel convertor which is configured to receive the fluid and produce the hydrogen rich fuel by the action of a bioenzyme on glucose in the fluid. The fluid that is fed and arranged to flow through the fuel generator 10 can be any one of cerebrospinal fluid (CSF), urine and glucose solution. CSF is a clear and colorless bodily fluid produced in the choroid plexus of the brain. CSF contains glucose and the apparatus 100 is arranged to use the glucose in the CSF to generate power. The glucose in CSF is D-glucose and the concentration of D-glucose in CSF is 400-850 mg/L. The fuel generator 10 is arranged to receive the CSF through a shunt tube 20 from a vessel in the human body that carries CSF. The shunt is a passage which allows movement of any fluid from one part of the body to another. The shunt tube 20 enables movement of CSF to the fuel generator 10. The shunt tube 20 can also be referred to as a cerebral shunt as the shunt tube 20 carries CSF. In an embodiment that uses urine as the fluid, the apparatus 100 is planted in proximity to the urinary bladder or the ureter such that urine from the urinary bladder or urine flowing into the urinary bladder is diverted into the apparatus 100 for power generation. The urine is supplied to the apparatus 100 through the shunt tube 20 from the urinary bladder or ureter. In this embodiment, the apparatus 100 utilizes the glucose in the urine. In another embodiment, glucose solution is used as the fluid and is transferred by the shunt tube to the apparatus 100. The mechanism of infusing and transporting the glucose solution is described hereinafter.

The apparatus 100 used with urine, glucose solution and CSF are the same and the method of working is also the same, which is described hereinafter. The apparatus 100 to be used with glucose solution comprises an additional component, which will be described hereinafter.

The low carbon fuel convertor which is the fuel generator 10 comprises a bioenzyme, which can be any one of pectine methyl esterase (PME) and zymase (yeast). Enzymes are biological molecules responsible for a multitude of chemical interconversions that are important for biological life. Among many biological functions carried out by enzymes in humans, some of them are the digestion of food and synthesis of DNA. The action of pectine methyl esterase on the fluid flowing through the fuel generator 10 yields methanol. The chemical formula of methanol is $CH_3OH$. It is apparent that methanol comprises 4 hydrogen atoms and 1 carbon atom. The hydrogen-carbon ratio which is depicted by H/C ratio is 4:1 for methanol. The action of zymase on the fluid flowing through the fuel generator 10 yields ethanol. The chemical formula of ethanol is $C_2H_5OH$. The reaction that occurs in the fuel generator 10 to convert glucose to ethanol using zymase is as follows:

It is apparent that ethanol comprises 6 hydrogen atoms and 2 carbon atoms. The H/C ratio for ethanol is 6:2. It is apparent that both in ethanol and methanol, the hydrogen content is greater than the carbon content and that forms the reason for ethanol and methanol to be referred to as a hydrogen rich fuel or a low carbon fuel.

Figure 2:
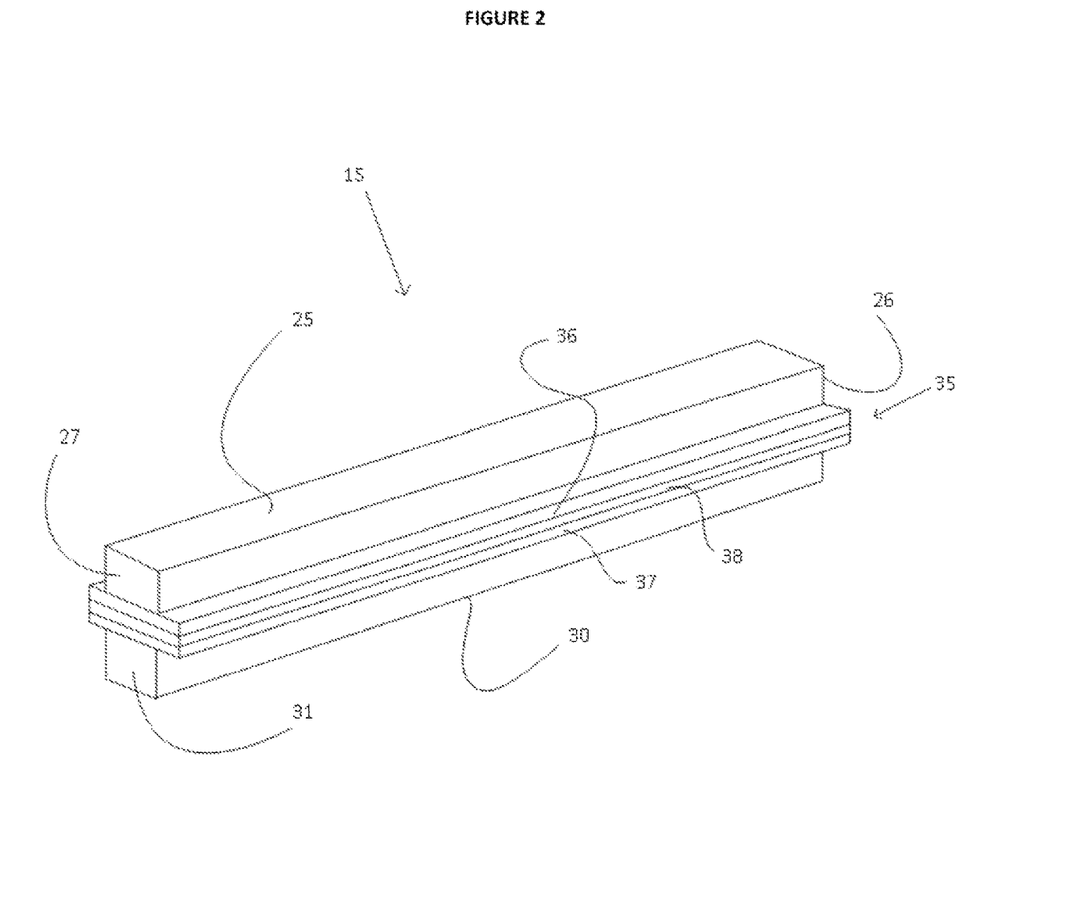
FIG. 2 is a schematic illustration of a bio fuel cell of the apparatus for in-vivo power generation of FIG. 1.

FIG. 2 is a schematic illustration of a biofuel cell of the apparatus 100. As illustrated in FIG. 2, the biofuel cell 15 comprises a first chamber 25 and a second chamber 30, separated by a membrane assembly 35. The first chamber 25 is a cathode chamber. The second chamber 30 is an anode chamber. The first chamber 25 comprises a first chamber entrance 26 and a first chamber exit 27. As illustrated in FIG. 1, a tube 40 departs from the shunt tube 20 carrying the fluid directly to the first chamber entrance 26 of the first chamber 25 of the biofuel cell 15. The shunt tube 20 is composed of silicone material. The tube 40 can also be referred to as a cathode chamber nanochannel.

The second chamber 30 or the anode chamber is arranged to receive the hydrogen rich fuel from the fuel generator 10 through a second chamber entrance 31. The hydrogen rich fuel is transported from the fuel generator 10 to the second chamber 30 through an anode chamber nanochannel 45 as illustrated in FIG. 1. As illustrated in FIG. 2, the membrane assembly 35 is an assembly comprising a first electrode 36, a second electrode 37 and a membrane 38. The first electrode 36 is a porous gas diffusion electrode (cathode) 36 and the second electrode 37 is a porous gas diffusion electrode (anode). The membrane 38 is a proton exchange membrane. The porous gas diffusion electrode (cathode) 36 can also be referred to as a cathode 36 for the purposes of explanation. The porous gas diffusion electrode (anode) 37 can also be referred to as an anode 37 for the purposes of explanation. The proton exchange membrane 38 can also be referred to as a polymer electrolyte membrane and is a semipermeable membrane, which is understood by a person skilled in the art. The proton exchange membrane 38 is disposed between the cathode 36 and the anode 37 forming a sandwich like structure. The proton exchange membrane comprises nafion, which is a sulfonated tetrafluoroethylene based fluoropolymer-copolymer. Nafion is used as a proton conductor in the proton exchange membrane. As described above, the cathode 36 and the anode 37 form part of the membrane assembly 35. The cathode 36 is open to a cavity (not shown in Figures) of the cathode chamber 25 and the anode 37 is open to a cavity (not shown in Figures) of the anode chamber 30. Both the cathode 36 and the anode 37 are made of Raney-platinum film. The cathode 36 is coated with a catalyst, which is capable of extracting oxygen from the fluid, when the fluid flows through the cavity of the first chamber 25. The fluid enters the first chamber 25 through the first chamber entrance 26 and as the fluid flows along the first chamber 25, oxygen is extracted from the fluid by the action of the catalyst laccase coated on the cathode. The oxygen generated in the first chamber 25 and the hydrogen from the hydrogen rich fuel in the second chamber 30 combine reactively across the membrane assembly 35 to result in a flow of electrons resulting in electricity. To elaborate, firstly the hydrogen ionizes and then diffuses through the proton exchange membrane 38 to combine with oxygen to form water. The half-cell reactions taking place are:

In the anode chamber 30, electrons are stripped from the hydrogen atoms at the anode 37. The positively charged hydrogen ions (protons) then pass through the proton exchange membrane 38 to the cathode 36, where they react with the oxygen and the stripped electrons to form water. The flow of electrons from the anode 37 to the cathode 36 results in electrical power to be supplied to in-vivo devices.

As illustrated in FIG. 2, the biofuel cell 15 is elongated with the first chamber 25, the second chamber 30 and the membrane assembly 35 between the first chamber 25 and the second chamber 30 being elongated. The first chamber entrance 26 and the second chamber entrance 31 are disposed at opposite ends of the biofuel cell 15, such that the fluid entering the first chamber entrance 26 and flowing through the first chamber 25 and the hydrogen rich fuel entering the second chamber entrance 31 and flowing through the second chamber 30 flow in opposite directions in the biofuel cell 15. As illustrated in FIG. 1, the fluid flowing out from the first chamber 25 and from which oxygen has been extracted flows out through a first nanochannel 50 to an exit nanochannel 55 through an intermediate nanochannel 60. The compositional remnants of the fluid from which hydrogen rich fuel has been generated in the fuel generator 10 passes to the exit nanochannel 55 through a second nanochannel 65. The compositional remnants of the hydrogen rich fuel from which hydrogen is extracted in the second chamber 30 along with water flows out through a third nanochannel 70. The third nanochannel 70 connects to the intermediate nanochannel 60 and drains into the intermediate nanochannel 60. The second nanochannel 65 from the fuel generator 10 and the intermediate nanochannel 60 meet and form the exit nanochannel 55. The exit nanochannel 55 drains into the abdominal cavity of the human being inside which the apparatus 100 is implanted.

The spatial and positional orientation of the apparatus 100 as illustrated in FIG. 1 enables the fluid to flow through the fuel generator 10 to produce the hydrogen rich fuel and the hydrogen rich fuel to flow through the second chamber 30 and the fluid directly through the first chamber 25 naturally aided by gravity, without the necessity for any powered fluid pumps. The oxygen and hydrogen in the cathode chamber 25 and the anode chamber 30 which is in gaseous form will be higher in volume when compared to the liquid form and will naturally be driven to diffuse through the membrane assembly 35, therefore running the biofuel cell 15.

In an exemplary embodiment of the apparatus 100, a width and a height of the first chamber 25 and the second chamber 30 are 500 nm and 500 nm respectively. A thickness of the cathode and the anode are 100 nm and 100 nm respectively. A length of the first chamber 25, the second chamber 30 and the membrane assembly 35 are 1000 nm, 1000 nm and 1000 nm respectively. A thickness of the membrane 38 is 100 nm. It is thus apparent from the above that the biofuel cell 15 is a nano-scale device and can thus be effectively and conveniently implanted in the human body.

As illustrated in FIG. 1, the apparatus 100 further comprises a packaging 75, the packaging composed on a biocompatible material such as bio glass. The chemical formula for bio glass is $Na_2O$—$CaO$—$SiO_2$—$P_2O_5$. The bio glass in the packaging 75 can be coated with polydimethysiloxane (PDMS). PDMS belongs to a group of polymeric organosilicon compounds. PDMS is optically clear, inert, non-toxic and non-flammable. PDMS is also referred to as silicone. The above mentioned properties of PDMS enable PDMS to be coated on the packaging 75 which is implanted inside the human body without any deleterious effects to the human body. The packaging and PDMS are hemocompatible and non-cytotoxic, in addition to exhibiting other biocompatible features. The bio glass packaging provides sturdy support to the package. The coating of PDMS as described above provides protection for the bio glass packaging 75 from various in-vivo forces. In other words, the coating of silicone reduces the brittleness of the packaging 75. The bio compatible material is not limited to what has been described above and can include other similar materials as well.

Figure 3:
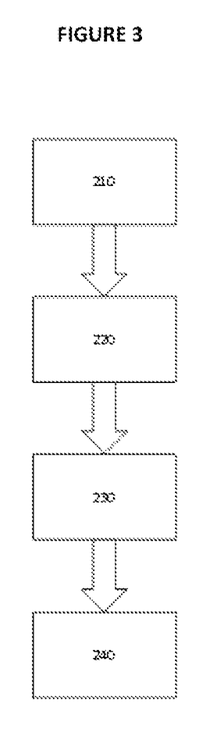
FIG. 3 is a flowchart showing the process steps for a method of in-vivo power generation in an in-vivo power generation apparatus.

FIG. 3 is a flowchart showing the process steps for a method 200 of in-vivo power generation using the in-vivo power generation apparatus 100. As illustrated in FIG. 3, the method 200 comprises a step 210 of generating the hydrogen rich fuel from the fluid by passing the fluid through the fuel generator 10, which has already been described earlier. The method 200 further comprises a step 220 of extracting oxygen from the fluid by passing the fluid through the first chamber 25 of the biofuel cell 15. The first electrode in the membrane assembly 35 is coated with a catalyst which enables extracting oxygen from the fluid. A further step 230 comprises passing the hydrogen rich fuel through the second chamber 30 in the biofuel cell 15. The method 200 comprises a further step 240 which comprises generating power by a reaction occurring across the membrane assembly 35, the membrane assembly 35 separating the first chamber 25 and the second chamber 30. The reaction occurs between the oxygen from the first chamber 25 and the hydrogen in the hydrogen rich fuel from the second chamber 30. The step 210 comprises utilizing a bioenzyme in the fuel generator 10 or the low carbon fuel convertor to act on glucose in the fluid to generate the hydrogen rich fuel, which can be one of ethanol and methanol.

The apparatus 100 for in-vivo power generation can be fabricated on a chip which can be implanted in the human body. The lifetime of the apparatus 100 described above can be 40000 to 60000 hours.

The CSF that is used as the fluid in the apparatus 100 and the method 200 can be any one of waste CSF and utilizable CSF. Waste CSF is CSF that is being drained out from the cerebral region through the thorax into the abdomen of the human body or the animal after being utilized in the cerebral region. Utilizable CSF is the CSF in the brain and which is still being utilized in the cerebral region. The apparatus 100 and method 200 can be implanted and employed in any part of the human body and animal and therefore utilizes CSF that is waste CSF or utilizable CSF depending on the implanted location.

Figure 4:
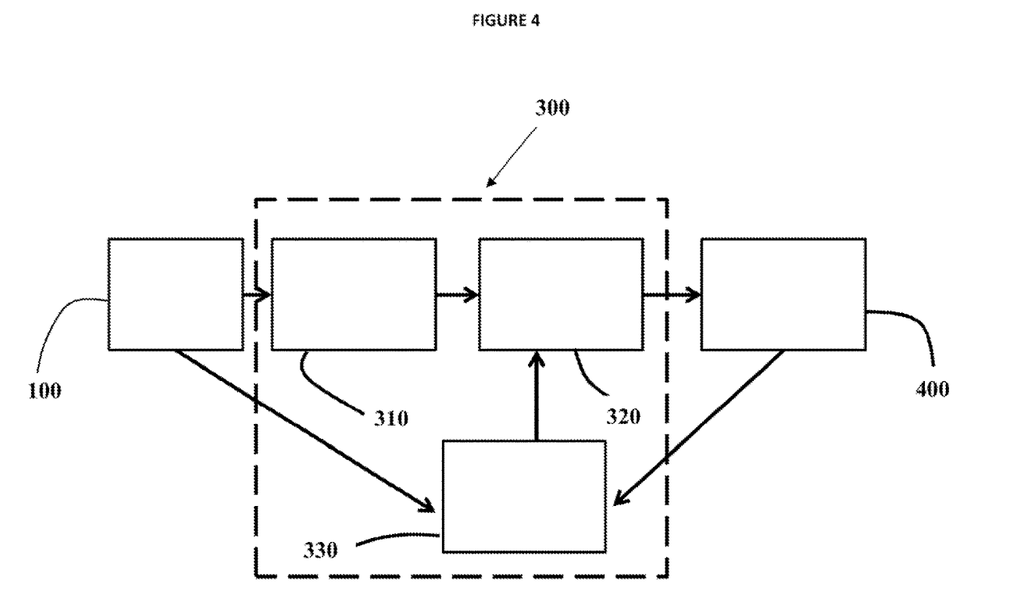
FIG. 4 is a schematic showing a conditioning unit interfacing the apparatus for in-vivo power generation and the body implant.

Moreover, the power generated by the fuel cell or apparatus 100 can be boosted or raised to be effectively utilized by the implant inside the body. FIG. 4 is a schematic showing a conditioning unit 300 interfacing the apparatus 100 for in-vivo power generation with the body implant. The power output generated by the above described fuel cell is in the order of 3-8 µW. This level of power output is conditioned by the conditioning unit 300. The conditioning unit 300 is also referred to as an ultra-low power conditioning circuit or ultra-low power conditioning unit. The power conditioned by the conditioning unit 300 is supplied to the body implant 400. The conditioning unit 300 comprises a step-up unit 310, a boost convertor unit 320 and a control unit 330.

Figure 5:
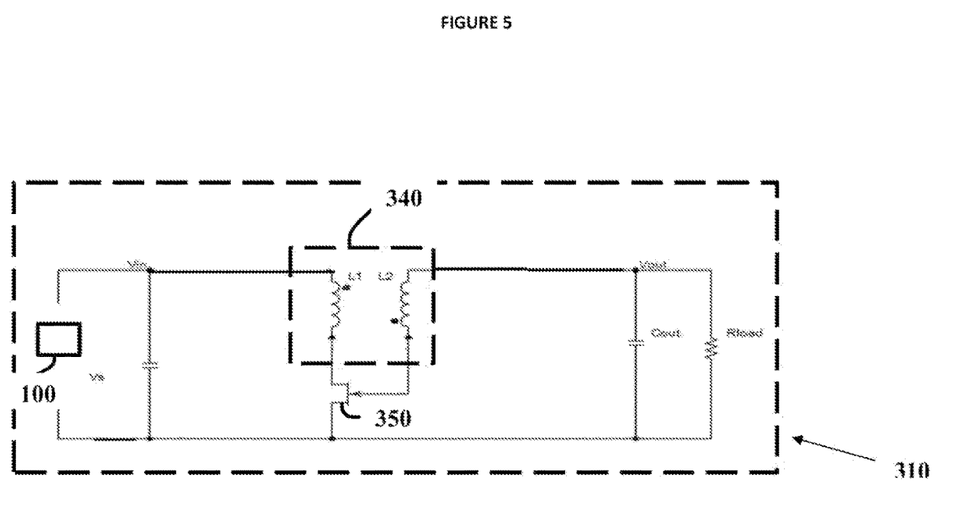
FIG. 5 shows a step-up unit forming a component of the conditioning unit of FIG. 4.

FIG. 5 shows the step-up unit 310. The step-up unit 310 comprises a step-up transformer 340 and a normally ON N-channel JFET transistor 350. Upon the apparatus 100 supplying the generated power to the step-up unit 310, the current increases in the primary winding of the step-up transformer 340. Consequently, the secondary winding applies a positive voltage on the gate of the JFET. As the JFET gate-source PN junction conducts, the output capacitor is charged with a negative voltage, thereby resulting in a negative output voltage. When the primary current reaches saturation, the voltage across the primary winding cancels and the negative voltage of the output capacitor is applied on the gate of the JFET pinching it off. The current in the primary winding decreases and a negative voltage is applied by the secondary winding on the gate of the JFET, resulting in the switching off of the JFET. The negative voltage falls back to zero and the oscillation process starts again. An example of JFET is 2N4338, which is characterized by a low gate-source cutoff voltage, which is from −0.5V to −1V. This characteristic of the JFET allows the boost convertor unit 320 to start-up with a small input voltage. The transformer turns-ratio is 1:20, which reflects a trade-off between efficiency and step-up ability.

Figure 6:
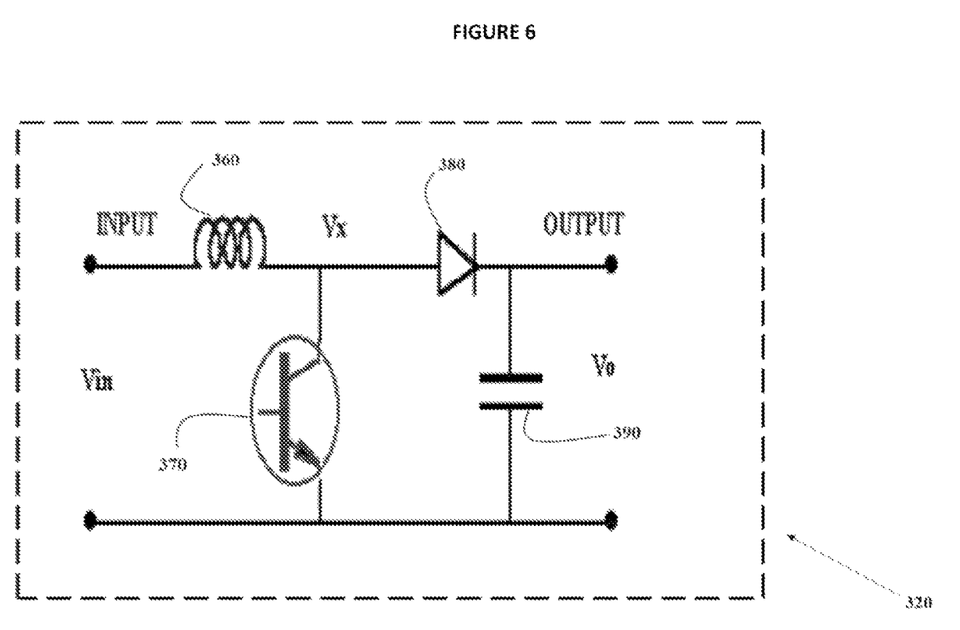
FIG. 6 shows a boost convertor unit of the conditioning unit of FIG. 4.

FIG. 6 shows the boost convertor unit 320 of the conditioning unit 300 of FIG. 4. The boost convertor 320 works on the principle of the tendency of an inductor to resist changes in current by creating and destroying a magnetic field. The boost convertor 320 comprises an inductor 360, a switch 370, a diode 380 and a capacitor 390. In a boost convertor, the output voltage is always higher than the input voltage. Upon closing the switch 370, current flows through the inductor 360 in clockwise direction and the inductor 360 stores some energy by generating a magnetic field. The polarity on the left side of the inductor in the circuit shown in FIG. 6 is positive. Upon opening the switch 370, current reduces as the impedance is higher. The magnetic field previously created is destroyed to maintain the current flow towards the load. The polarity is thus reversed. Consequently, two sources will be in series causing a higher voltage to charge the capacitor through the diode 380. If the switch 370 is cycled fast enough, the inductor 360 will not discharge fully in between charging stages, and the load will always see a voltage greater than that of the input source alone when the switch 370 is opened. Also when the switch 370 is opened, the capacitor 390 in parallel with the load is charged to the combined voltage. Upon closing the switch 370 and the right side of the boost convertor circuit is shorted from the left side, the capacitor 390 is therefore able to provide the voltage and energy to the load. During this time, the diode 380 prevents the capacitor 390 from discharging through the switch 370. Opening the switch 370 fast enough prevents the capacitor 390 from discharging too much or a lot.

The control circuit 330 comprises an ultra-low power microprocessor such as MSP-430 or anything similar. The control circuit 330 receives information from the body implant 400 with regards to power requirement, duration and other such related things. The control circuit 330 communicates with the boost convertor 320 to supply power to the implant with the desired characteristics.

The advantage of the conditioning unit 300 is that the conditioning unit boosts or raises the low voltage power generated by the fuel cell to a higher voltage level and also manages the power requirement and distribution so as to be effectively utilized by the implant in the body.

Figure 7:
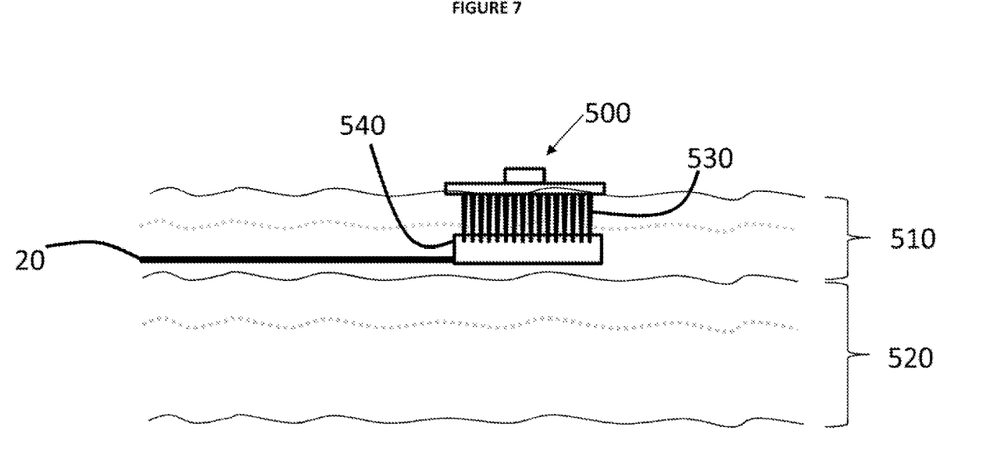
FIG. 7 shows a schematic of a transdermal glucose reservoir implanted in an epidermal layer of a user.

FIG. 7 shows a schematic of a transdermal glucose reservoir 500 implanted in an epidermal layer of a user that uses the apparatus 100. As illustrated in FIG. 7, the skin shows epidermis 510 and dermis 520. The reservoir 500 is implanted on the epidermal layer 510. The reservoir 500 can be connected to an external supply of glucose solution or can be arranged to store glucose solution temporarily. The reservoir 500 comprises a plurality of micro needles 530 for delivery of glucose solution to the shunt tube to be delivered to the apparatus 100. The plurality of micro needles 530 empty the glucose solution to a trough 540 which is connected to the shunt tube for transporting to the apparatus 100.

It is to be understood that the foregoing description is intended to be purely illustrative of the principles of the disclosed techniques, rather than exhaustive thereof, and that changes and variations will be apparent to those skilled in the art, and that the present invention is not intended to be limited other than as expressly set forth in the following claims.

I claim:

1. An apparatus for in-vivo power generation comprising:
   a fuel generator arranged to produce a hydrogen rich fuel from a liquid flowing through the fuel generator, wherein the fuel generator is a low carbon fuel convertor which is configured to receive the liquid and produce the hydrogen rich fuel by the action of a bioenzyme on glucose in the liquid; and
   a biofuel cell fluidically coupled to the fuel generator, the biofuel cell including a first chamber and a second chamber separated by a membrane assembly, wherein the membrane assembly comprises a first electrode having a catalyst for enabling extraction of oxygen from the liquid, a second electrode, and a membrane, the liquid being configured to flow through the first chamber, and wherein the second chamber is arranged to receive the hydrogen rich fuel from the fuel generator,
   wherein, when in use, electrical power is generated when the oxygen from the first chamber and hydrogen in the hydrogen rich fuel from the second chamber combine reactively.

2. The apparatus for in-vivo power generation as claimed in claim 1, wherein the liquid is one of cerebro spinal fluid, glucose solution or urine.

3. The apparatus for in-vivo power generation as claimed in claim 2, further comprising a transdermal glucose reservoir implanted on an epidermal layer of a user of the apparatus, wherein the transdermal glucose reservoir comprises a plurality of micro needles for delivery of glucose solution to the fuel generator and the biofuel cell.

4. The apparatus for in-vivo power generation as claimed in claim 2, wherein a quantity of hydrogen is greater than a quantity of carbon in the hydrogen rich fuel.

5. The apparatus for in-vivo power generation as claimed in claim 1, wherein the first electrode is a cathode.

6. The apparatus for in-vivo power generation as claimed in claim 5, wherein the catalyst is laccase.

7. The apparatus for in-vivo power generation as claimed in claim 1, wherein the hydrogen rich fuel is one of ethanol or methanol.

8. The apparatus for in-vivo power generation as claimed in claim 1, wherein the bioenzyme is one of pectine methyl esterase or zymase.

9. The apparatus for in-vivo power generation as claimed in claim 1, wherein the bio fuel cell is a nano scale device.

10. The apparatus for in-vivo power generation as claimed in claim 1, wherein the membrane is nafion.

11. The apparatus for in-vivo power generation as claimed in claim 10, wherein a thickness of the membrane is 100nm.

12. The apparatus for in-vivo power generation as claimed in claim 1, further comprising a packaging for the bio fuel cell, the packaging composed of bio compatible material.

13. The apparatus for in-vivo power generation as claimed in claim 12, wherein the bio compatible material comprises bio glass, the bio glass coated with polydimethylsiloxane.

14. The apparatus for in-vivo power generation as claimed in claim 1, further comprising a conditioning unit interfacing the biofuel cell and a body implant to condition the power generated by the biofuel cell to be supplied to the body implant.

15. The apparatus for in-vivo power generation as claimed in claim 14, wherein the conditioning unit comprises a step-up unit, a boost convertor unit and a control unit.

* * * * *